(12) United States Patent
Jeong

(10) Patent No.: US 9,943,497 B2
(45) Date of Patent: Apr. 17, 2018

(54) PHARMACEUTICAL COMPOSITION FOR PREVENTING OR TREATING PULMONARY FIBROSIS

(71) Applicants: GACHON UNIVERSITY OF INDUSTRY-ACADEMIC COOPERATION FOUNDATION, Gyeonggi-do (KR); GIL MEDICAL CENTER, Incheon (KR)

(72) Inventor: Sung Hwan Jeong, Seoul (KR)

(73) Assignees: GACHON UNIVERSITY OF INDUSTRY-ACADEMIC COOPERATION FOUNDATION, Gyeonggi-Do (KR); GIL MEDICAL CENTER, Incheon (KR)

( * ) Notice: Subject to any disclaimer, the term of this patent is extended or adjusted under 35 U.S.C. 154(b) by 0 days.

(21) Appl. No.: 14/130,389

(22) PCT Filed: Nov. 8, 2013

(86) PCT No.: PCT/KR2013/010143
§ 371 (c)(1),
(2) Date: May 20, 2016

(87) PCT Pub. No.: WO2014/185607
PCT Pub. Date: Nov. 20, 2014

(65) Prior Publication Data
US 2016/0287547 A1    Oct. 6, 2016

(30) Foreign Application Priority Data

May 15, 2013 (KR) ........................ 10-2013-0055347

(51) Int. Cl.
*A61K 31/26* (2006.01)
*A61K 31/155* (2006.01)

(52) U.S. Cl.
CPC ............ *A61K 31/26* (2013.01); *A61K 31/155* (2013.01)

(58) Field of Classification Search
CPC ............................. A61K 31/26; A61K 31/155
(Continued)

(56) References Cited

U.S. PATENT DOCUMENTS

| 2006/0020046 | A1 | 1/2006 | Goralczyk | |
| 2010/0260733 | A1* | 10/2010 | Qi | A61K 8/49 424/93.43 |
| 2011/0250300 | A1* | 10/2011 | Biswal | A01K 67/027 424/752 |

FOREIGN PATENT DOCUMENTS

WO    2008101692    8/2008

OTHER PUBLICATIONS

Lim et al, J. Cellular Physiology (2012), vol. 227 (3), pp. 1081-1089.*

(Continued)

*Primary Examiner* — Craig D Ricci
(74) *Attorney, Agent, or Firm* — Gottlieb, Rackman & Reisman, P.C.

(57) ABSTRACT

The present invention relates to a pharmaceutical composition for preventing or treating pulmonary fibrosis comprising an isothiocyanate-based compound and a biguanide agent as active ingredients, a method for preventing or treating pulmonary fibrosis using the composition, and use of the isothiocyanate-based compound and the biguanide agent for the preparation of the prophylactic or therapeutic agent for preventing or treating pulmonary fibrosis. The pharmaceutical composition comprising the isothiocyanate-based compound and the biguanide agent as active ingredients of the present invention can be used to stably prevent or treat pulmonary fibrosis for which specific therapeutic (Continued)

agents have not yet been known, and thus it can be widely used for health and welfare improvement through treatment of pulmonary fibrosis.

10 Claims, 4 Drawing Sheets

(58) Field of Classification Search
USPC .......................................................... 514/515
See application file for complete search history.

(56) References Cited

OTHER PUBLICATIONS

Cufi et al, Cell Cycle (2010), vol. 9 (22), pp. 4461-4468.*
Elise Artaud-Macari et al, European Respiratory Journal (2011), vol. 38, pp. 175.*
Kyunci, Seon Yeong et al. "Effect of Isothlocyanate and Biguanide derived from Bleomycin for Pulmonary Fibrosis Mouse Model", The Korean Academy of Tuberculosis and Respiratory Diseases, Abstract of Fall Conference Presentation, 2012, vol. 114, p. 246.
International Search Report for PCT/KR2013/010142, dated Jan 20, 2014.

* cited by examiner

Drawings
[Figure 1a]
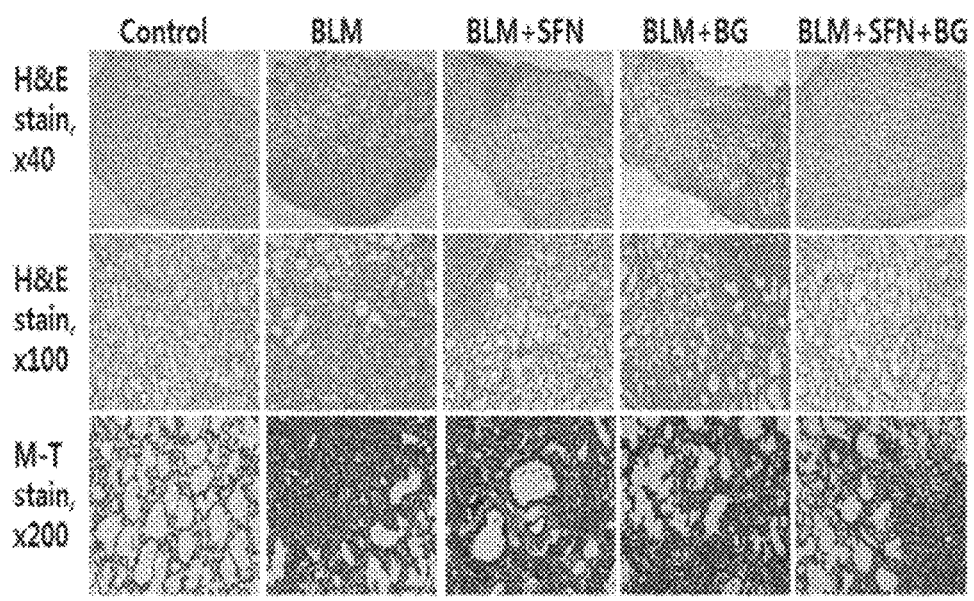

[Figure 1b]
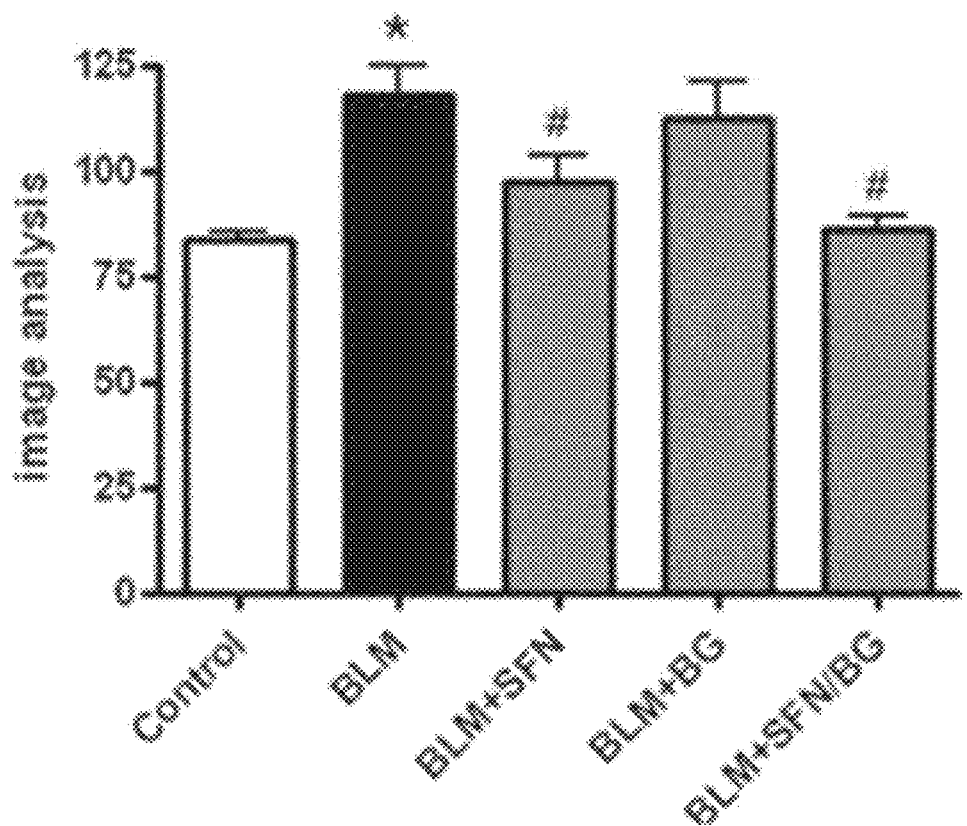
\*\*\*,\*\* and \* denote P<0.001, P<0.01 and P<0.05, respectively, Statistically significant compared with control group.
,## and # denote P<0.001, P<0.01 and P<0.05, respectively, Statistically significant compared with BLM group.

[Figure 1c]
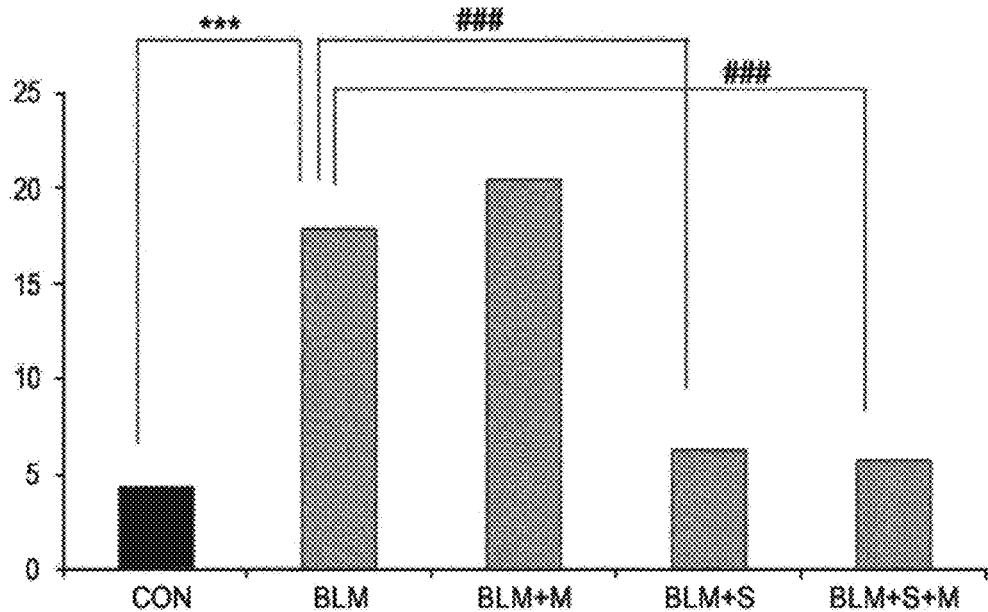
*, and * denote P<0.001, P<0.01 and P<0.05, respectively, Statistically significant compared with control group.
,## and # denote P<0.001, P<0.01 and P<0.05, respectively, Statistically significant compared with BLM group.
[Figure 2]
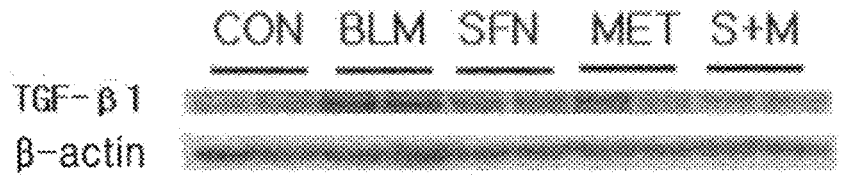

[Figure 3]
[Figure 4]
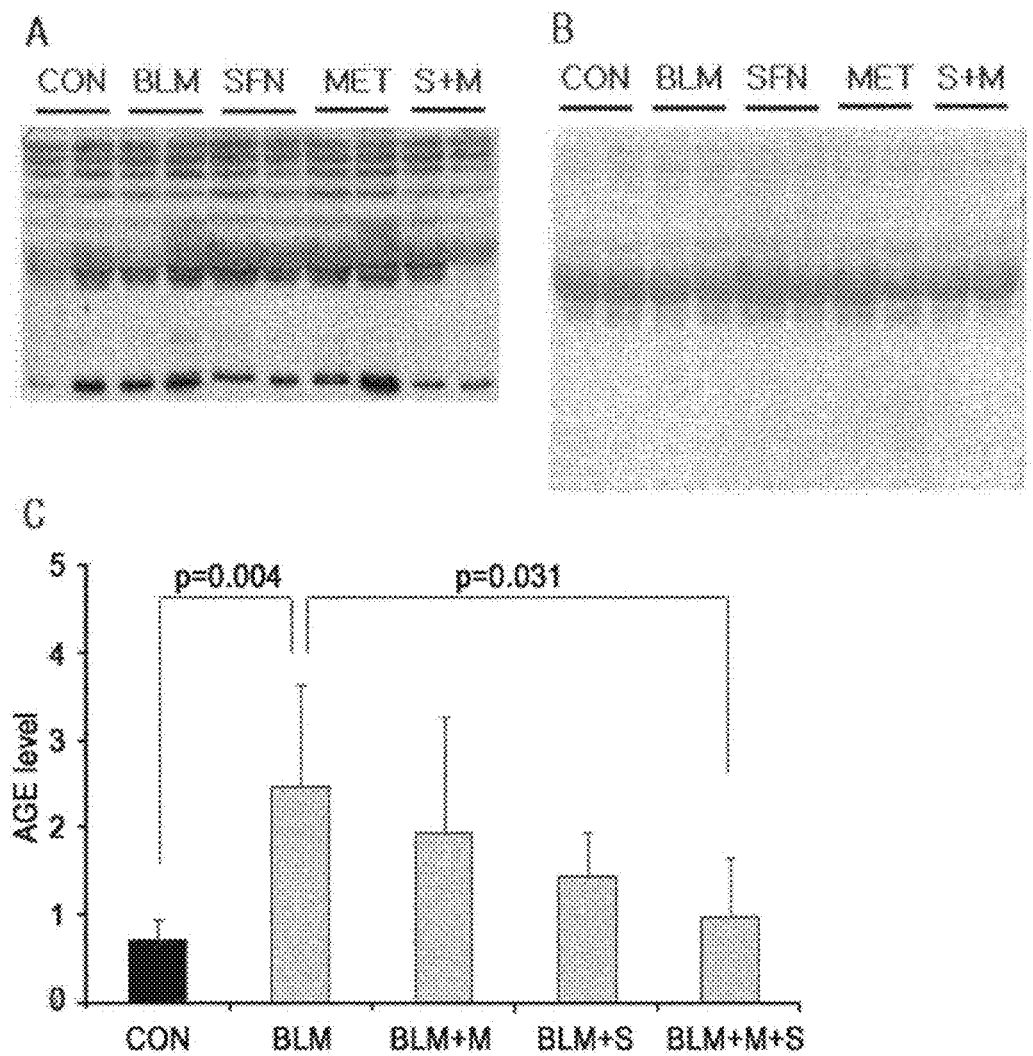

PHARMACEUTICAL COMPOSITION FOR PREVENTING OR TREATING PULMONARY FIBROSIS

BACKGROUND OF THE INVENTION

1. Field of the Invention

The present invention relates to a pharmaceutical composition for preventing or treating pulmonary fibrosis. More particularly, the present invention relates to a pharmaceutical composition for preventing or treating pulmonary fibrosis comprising an isothiocyanate-based compound and a biguanide agent as active ingredients, a method for preventing or treating pulmonary fibrosis using the composition, and use of the isothiocyanate-based compound and the biguanide agent for the preparation of the prophylactic or therapeutic agent for preventing or treating pulmonary fibrosis.

2. Description of the Related Art

Idiopathic pulmonary fibrosis (IPF) is a chronic disease without any apparent etiology, characterized by a progressive fibrosis of the lung interstitium. This disease is generally confined to the lung and has the histological pattern of usual interstitial pneumonia (UIP). There are differences between reports, but this disease is known to have a prevalence of 2-29 cases per 100,000 individuals. In Korea, IPF is designated as one of the rare and intractable diseases, and its clinical coarse is variable. Generally, IPF progresses to respiratory failure with a slowly progressive decline in lung function, and is a fatal disease with a median survival time of 2-3 years from the time of diagnosis. For this reason, many attempts have been made to reveal the exact pathogenesis and etiology of IPF and to develop a therapeutic agent, but no effective therapeutic agents are available so far.

The pathogenesis of IPF is still unclear, but current concepts suggest that repetitive damage of alveolar epithelial cells is followed by an aberrant healing response, resulting in pulmonary fibrosis. The damage to alveolar epithelial cells resulting from various stimulations is not easily regenerated, and aberrant activation of myofibroblasts occurs during the healing process of the damage, leading to excessive production of extracellular matrix and consequently, interstitial pulmonary fibrosis. Once this pathological mechanism was revealed, the use of anti-fibrotic agents was attempted rather than anti-inflammatory agents which were considered as a classical IPF therapy. If has been also suggested that increased oxidative stress is one of the important causes of IPF, which was demonstrated in many pulmonary fibrosis-induced experimental models. An antioxidant N-acetylcysteine is also considered as a therapeutic drug for IPF, although there are restrictions on the use thereof.

According to the 2011 ATS/ERS/JRS/ALAT guidelines for IPF, a combination therapy of an immunosuppressant azathioprine and an anti-inflammatory agent corticosteroid rather increases mortality. Thus, N-acetylcysteine monotherapy or treatment with anticoagulation or pirfenidione (anti-inflammatory, anti-fibrotic, and antioxidant effects) may be a reasonable choice in the minority of patients with IPF. In addition, long-term oxygen treatment or lung transplantation is recommended in the case of chronic respiratory failure. None of the representative anti-inflammatory agents such as corticosteroid or immunosuppressants such as azathioprine, cyclosporin A, and cyclophosphamide are recommended for the treatment. Further, IFN-γ and bosentan have been tried as an anti-fibrotic agent and did not show therapeutic effects. There is a need for a new therapeutic agent for IPF which exhibits various action mechanisms such as anti-inflammatory, anti-fibrotic, and antioxidant effects rather than one action mechanism.

The present inventors have made many efforts to develop a pharmaceutical composition capable of exhibiting a specific prophylactic or therapeutic effect on pulmonary fibrosis. As a result, they found that a combined formulation of an isothiocyanate-based compound, sulforaphane and a biguanide agent, metformin, shows a therapeutic effect on pulmonary fibrosis, thereby relatively completing the present invention.

SUMMARY OF THE INVENTION

An object of the present invention is to provide a pharmaceutical composition showing a prophylactic or therapeutic effect on pulmonary fibrosis.

Another object of the present invention is to provide a method for preventing or treating pulmonary fibrosis using the composition.

Still another object of the present invention is to provide use of an isothiocyanate-based compound and a biguanide agent for the preparation of the pharmaceutical composition.

BRIEF DESCRIPTION OF THE DRAWINGS

FIG. 1a is a microscopic image at magnification of 40× or 100× after H&E staining and a microscopic image at magnification of 200× after Masson-trichrome (M-T) staining of the lung tissues of the experimental animals that were induced to have pulmonary fibrosis and administered with each of the therapeutic agents, respectively;

FIG. 1b is a graph showing the result of quantitative analysis of the damaged fibrotic tissue level in each long tissue after H&E staining of the lung tissues of the experimental animals that were induced to have pulmonary fibrosis and administered with each of the therapeutic agents;

FIG. 1c is a graph showing the result of quantitative analysis of the damaged fibrotic tissue level in each lung tissue after Masson-trichrome (M-T) staining of the lung tissues of the experimental animals that were induced to have pulmonary fibrosis and administered with each of the therapeutic agents;

FIG. 2 is a photograph showing the result of Western blot analysis for TGF-β1 in the lung tissue samples and the serum samples of the experimental animals that were induced to have pulmonary fibrosis and administered with each of the therapeutic agents;

FIG. 3 is a photograph showing the result of Western blot analysis for fibronectin in the lung tissue samples and the serum samples of the experimental animals that were induced to have pulmonary fibrosis and administered with each of the therapeutic agents; and FIG. 4 is a photograph (A) showing the results of Western blot analysis and ELISA, a photograph (B) showing the results of Western blot analysis and Ponceau staining, and a graph (C) showing the result of ELISA for AGE in the lung tissue samples and the serum samples of the experimental animals that were induced to have pulmonary fibrosis and administered with each of the therapeutic agents, respectively.

DETAILED DESCRIPTION OF THE PREFERRED EMBODIMENTS

In one aspect to achieve the above described objects of the present invention, the present invention provides a pharmaceutical composition for preventing or treating pulmonary fibrosis comprising an isothiocyanate (ITC)-based compound and a biguanide agent as active ingredients.

The present inventors nave conducted many studies to develop therapeutic agents capable of preventing or treating pulmonary fibrosis which is a rare and intractable disease and for which a specific medicine has not yet been known. As a result, they have paid attention to sulforaphane and metformin that are known as natural anticancer agents. Sulforaphane is one of the isothiocyanate (ITC)-based compounds, and shows an inhibitory effect on tumor cell proliferation by inhibiting phosphatidylinositol 3-kinase (PI3K)/Akt signal transduction pathway. Metformin is one of the biguanide (BG) agents, and shows an inhibitory effect on tumor cell proliferation by inhibiting mTOR (mammalian target of rapamycin). Because both tumor cells and fibrotic lung tissues are similar in terms of being cell proliferative acquired irreversible tissues, it was expected that sulforaphane or metformin will show a specific prophylactic or therapeutic effect on pulmonary fibrosis.

Accordingly, the present inventors treated sulforaphane and metformin to the pulmonary fibrosis-induced animal models. As a result, they found that sulforaphane or metformin slightly alleviated pulmonary fibrosis or snowed therapeutic effects. However, these effects were found to be slightly unstable. Therefore, it was examined, whether co-treatment of the pulmonary fibrosis-induced animal models with sulforaphane and metformin is able to show synergistic effects. Consequently, it was found that pulmonary fibrosis can be stably treated by the co-treatment of sulforaphane and metformin.

As used, herein, the term "isothicoyanate (ITC)-based compound" means one of the compounds collectively called mustard oil found in various mustards as a natural source, and it has been known as a pungent spice traditionally used in foods. Representative examples thereof include allylmustard oil (allyl isotniocyanate), sulforaphane or the like. With respect to the objects of the present invention, the ITC compound is used as an active ingredient that is included in the pharmaceutical composition for preventing or treating pulmonary fibrosis, and a specific compound thereof may be exemplified by sulforaphane, but is not limited thereto. All kinds of ITC compounds showing the prophylactic or therapeutic effect on pulmonary fibrosis can be used.

As used hereon, the term "sulforaphane (SFN)" is one of the isocyanates that are abundant in cruciferous vegetables such as cabbage, broccoli, Brussels sprouts, cauliflower, kale, bok choy (Chinese green cabbage), arugula, collards (kale variety), kohlrabi, mustard, turnip, red radish, watercress or the like, and means a compound having a chemical formula of $C_6H_{11}NOS_2$ and a molecular weight of 177.29. Sulforaphane can be generated from hydrolysis of glucosinolate having a strong antioxidant effect by myrosinase in the process of digestion, and shows an excellent antioxidant effect, an anticancer effect, a bactericidal effect against Helicobacter pylori, and an inhibitory effect, on inflammatory factor activation. In particular, its anticancer activity is known to be attributed, to inhibition of tumor cell proliferation by inhibiting phosphatidylinositol 3-kinase (PI3K)/Akt signal transduction pathway.

As used herein, the term "biguanide (BG) agent" is a compound having a chemical formula of $C_2H_7H_5$ and a molecular weight of 101.11, and means a compound having a pharmaceutical use, among the biguanide derivatives obtained by substituting functional groups of biguanide compounds. The known BG agents are metformin, phenformin, buformin, proguanil or the like. With respect to the objects of the present invention, the BG agent is used as an active ingredient that is included in the pharmaceutical composition for preventing or treating pulmonary fibrosis, and a specific compound thereof may be exemplified by metformin, but is not limited thereto. Any kind of EG agent that shows a prophylactic or therapeutic effect on pulmonary fibrosis can be used.

As used herein, the term "metformin (Met)" means a compound of the BG agents, which has a chemical formula of $C_4H_{11}N_5$ and a molecular weight of 129.16. Metformin is used as a strong therapeutic agent for insulin non-dependent diabetes, and its major pharmacological actions are known to be an inhibitory effect on hepatic gluconeogenesis, an effect of reducing the sugar absorption rate in the stomach and the blood glucagon level, and an effect of facilitating glycolysis in the tissue to stimulate intestinal conversion of glucose to lactate. Therefore, metformin can be used in the treatment of obesity as well as insulin non-dependent diabetes. In addition to these major effects, metformin is known to have an inhibitory effect on proliferation of cancer stem ceils inducing carcinogenesis. In most cancers, AMPK (AMP-activated protein kinase) is inactivated, the enzyme inhibits excessive ATP production by supplying excessive glucose to mitochondria. Metformin activates the AMPK enzyme to inactivate cancer proliferation enzyme (mTOR) that is activated in cancer cells, leading to inhibition of cancer stem cell proliferation.

As used herein, Idiopathic pulmonary fibrosis is one of the chronic interstitial lung diseases, characterized by change of the lung tissue to fibrous tissue and this disease causes dyspnoea, coughing, cyanoderma, finger clubbing or the like. In histological examination, honeycombed or atypical fibrous cell populations and UIP pattern are observed. Until now, therapeutic agents such as steroids, interferon gamma, acetyl cysteine, pirfenidone, bosentan or the like have been used, but specific therapeutic effects have not been reported yet.

According to one embodiment of the present invention, in order to induce pulmonary fibrosis, C57BL/6 mice were administered with Bleomycin (BLM) to prepare pulmonary fibrosis-induced animal models. These animal models were treated with one of isothiocyanate (ITC)-based compounds, sulforaphane (SFN) and one of biguanide (BG) agents, metformin (Met) singly or in combination (Example 1). As a result, histological findings confirmed that the increased fibrous tissue by BLM treatment showed the lowest level in the lung tissues treated with combinations of SFN and Met, indicating improvement of pulmonary fibrosis (FIGS. 1a to 1c), and the lung tissues co-treated with SFN and Met showed the lowest levels of TGF-β1 (transforming growth factor β1) (FIG. 2), fibronectin (FIG. 3) and AGE (advanced glycation end products) (FIG. 4) which are known as pulmonary fibrosis markers.

Therefore, the composition for preventing or treating pulmonary fibrosis of the present invention includes the isothiocyanate-based compound and the biguanide agent as active ingredients. In this regard, the isothiocyanate-based compound may be, but is not particularly limited to, preferably sulforaphane, and the biguanide agent may be, but is not particularly limited to, preferably metformin.

The pharmaceutical composition of the present invention may further include a pharmaceutically acceptable diluent, ezcipient, or carrier. The composition comprising the pharmaceutically acceptable carrier may be formulated in a wide variety of oral or parenteral dosage forms. Such formulations may be prepared using diluents or ezcipients ordinarily employed, such as a filler, an extender, a bindery a wetting agent, a disintegrating agent, a surfactant or the like. Examples of a solid formulation for oral administration include a tablet, a pill, a powder, a granule, and a capsule, and the solid formulation may be prepared by mixing one or more compounds with at least one excipient, for example, starch, calcium carbonate, sucrose, lactose, gelatin or the like. Further, in addition to the simple excipients, lubricants such as magnesium stearate, talc or the like may be used. Examples of a liquid formulation for oral administration include a suspension, a liquid for internal use, an emulsion, a syrup or the like, and various excipients such as a wetting agent, a sweetener, a flavor, a preservative or the like may be included, in addition to general diluents such as water and liquid paraffin. Examples of the formulation for parenteral administration include an aseptic aqueous solution, a non-aqueous solvent, a suspension, an emulsion, a lyophilized agent, and suppository. As the non-aqueous solvent and suspension, propylene glycol, polyethylene glycol, plant oil such as olive oil, injectable ester such as ethyloleate may be used. As a suppository base, witepsol, macrogol, tween 61, cacao butter, lauric butter, glycerogelatin or the like may be used.

The pharmaceutical composition may have any one formulation selected from the group consisting of a tablet, a pill, a powder, a granule, a capsule, a suspension, a liquid for internal use, an emulsion, a syrup, an aseptic aqueous solution, a non-aqueous solvent, a suspension, an emulsion, a lyophilized agent, and suppository.

In another aspect to achieve the above described objects of the present invention, the present invention provides a method for preventing or treating pulmonary fibrosis, comprising the step of (a) administering the pharmaceutical composition for preventing or treating pulmonary fibrosis comprising the isothiocyanate-based compound and the biguanide agent as active ingredients to a subject who is suspected of having pulmonary fibrosis or has pulmonary fibrosis; or (b) administering the pharmaceutical composition comprising the isothiocyanate-based compound and the pharmaceutical composition comprising the biguanide agent sequentially or in reverse order or simultaneously to a subject who is suspected of having pulmonary fibrosis or has pulmonary fibrosis. In this regard, the active ingredients included in each composition are the same as described above.

The method for preventing or treating pulmonary fibrosis provided in the present invention is performed to induce the synergistic therapeutic effect of the isothiocyanate-based compound and the biguanide agent. Therefore, administration of the pharmaceutical composition comprising both the isothiocyanate-based compound and the biguanide agent may be performed, or individual administrations of the pharmaceutical composition comprising the isothiocyanate-based compound and the pharmaceutical composition comprising the biguanide agent may be performed. When the individual administrations of the pharmaceutical composition comprising the isothiocyanate-based compound and the pharmaceutical composition comprising the biguanide agent are performed, the pharmaceutical composition comprising the isothiocyanate-based compound, may be first administered and subsequently, the pharmaceutical composition comprising the biguanide agent may be administered, or the pharmaceutical composition comprising the biguanide agent may be first administered and subsequently, the pharmaceutical composition comprising the isothiocyanate-based compound may be administered, or the pharmaceutical composition comprising the isothiocyanate-based compound and the pharmaceutical composition comprising the biguanide agent may be administered at the same time. At this time, the pharmaceutical composition comprising the isothiocyanate-based compound may be a pharmaceutical composition comprising allyl mustard oil (allyl isothiocyanate), sulforaphane or the like, as described above, and the pharmaceutical composition comprising the biguanide agent may be a pharmaceutical composition comprising metformin, phenformin, buformin, proguanil or the like, as described, above. Also, when the pharmaceutical composition comprising the isothiocyanate-based compound and the pharmaceutical composition comprising the biguanide agent are administered individually, dosal ratio of the pharmaceutical composition comprising the isothiocyanate-based compound, and the pharmaceutical composition comprising the biguanide agent may be, but is not particularly limited, to, preferably 1:200 to 1:600 (w/w), based on the weight of active ingredients.

As used herein, the term "subject" means all animals comprising human having pulmonary fibrosis or being suspected of having pulmonary fibrosis.

In the present invention, the pharmaceutical composition may be administered via any of the common routes, as long as it is able to reach a desired tissue. The pharmaceutical composition of the present invention may be administered via an intraperitoneal, intravenous, intramuscular, subcutaneous, intradermal, oral, intranasal, intrapulmonary or intrarectal route depending on the desired purpose, but is not limited thereto. In addition, the pharmaceutical composition may be administered, by any device capable of delivering the active ingredient to the target cell.

The pharmaceutical composition according to one embodiment of the present invention includes sulforaphane and metformin. The mixing ratio of sulforaphane and metformin included in the composition may be, but is not particularly limited to, 1:200 to 1:600 (w/w), and preferably 1:500 (w/w). The content of sulforaphane in the composition may be, but is not particularly limited to, 0.0001 to 0.1% by weight, based, on the total weight of the final composition. The content of metformin in the composition may be, but is not particularly limited to, 0.02 to 60% by weight, based on the total weight of the final composition. The content, of the mixed formulation of sulforaphane and metformin in the composition may be, but is not particularly limited to, 0.01 to 70% by weight, based on the total weight of the final composition.

The pharmaceutical composition of the present invention may be administered in a pharmaceutically effective amount, and as used herein, the phrase "pharmaceutically effective amount" refers to an amount sufficient to treat the disease at a reasonable benefit/risk ratio applicable to any medical treatment. An effective dose level may be determined depending on a variety of factors comprising the type, severity, age, and sex of the subject, drug activity, drug sensitivity, administration time, administration route, discharge ratio, treatment period, and co-administered drugs, and other factors well known in the medical field. The pharmaceutical composition of the present invention may be administered alone or in combination with other therapeutics. The co-administration of the pharmaceutical composition of the present invention with the conventional therapeutics may be carried out sequentially or simultaneously. Single or multiple dosages are possible. It is important to use the composition in the minimum possible amount sufficient to obtain the greatest therapeutic effect without side effects, considering all the factors.

The administration dose of the pharmaceutical composition for preventing or treating pulmonary fibrosis of the present invention may be determined by those skilled in the art considering purpose of use, severity of the disease, the age, body weight, sex, and anamnesis of the subject, or the type of the substance used as the active ingredient. In one embodiment, the composition comprising the mixed formulation of sulforaphane and metformin of the present invention may be administered in a dose of approximately 1 μg/kg/day to 100 mg/kg/day, and preferably 20 to 30 mg/kg/day for an adult. In another embodiment, when the pharmaceutical composition comprising sulforaphane and the pharmaceutical composition comprising metformin are administered individually, the pharmaceutical composition comprising sulforaphane may be administered in a dose of approximately 1 to 200 μg/kg/day, and preferably 50 to 100 μg/kg/day for an adult, and the pharmaceutical composition comprising metformin may be administered in a dose of approximately 10 to 100 mg/kg/day, and preferably 20 to 30 mg/kg/day for an adult. The administration frequency of the pharmaceutical composition may be, but is not limited to, once day or several times a day divided.

In still another aspect to achieve the above; described objects of the present invention, the present invention provides use of the isothiocyanate-based compound and the biguanide agent for the preparation of the prophylactic or therapeutic agent for pulmonary fibrosis.

As described above, the present inventors first demonstrated that co-administration of the isothiocyanate-based compound and the biguanide agent is able to restore the lung tissues of the pulmonary fibrosis-induced animals to the improving conditions, and therefore, the isothiocyanate-based compound and the biguanide agent can be used as active ingredients in the preparation of the prophylactic or therapeutic agent for pulmonary fibrosis. The diluent, excipient, or carrier used in the preparation of the formulation are the same as described above, and, the contents of the isothiocyanate-based compound and the biguanide agent in the formulation are also the same as described above, and the method used in the preparation of the formulation may be a method known in the art.

Hereinafter, the present invention will be described in more detail with reference to Examples. However, these Examples are for illustrative purposes only, and the invention is not intended to be limited by these Examples.

Example 1: Preparation of Experimental Animals Induced to have Pulmonary Fibrosis and Administered with Each of Therapeutic Agents It was intended, to examine the therapeutic effects of sulforaphane (SFN) and biguanide (BG) on pulmonary fibrosis that was induced by administration of Bleomycin (BLM) under in vivo conditions.

In detail, C57BL/6 mice were administered with combination of BLM, SFN and metformin (Met) which is one of BG agents, and control groups and experimental groups were prepared: a control group that was orally administered with sterile physiological saline (SA) and orally administered with distilled water; an experimental group (BLM) that was administered with BLM and orally administered with distilled water; an experimental group (BLM+SFN) that was administered with BLM and orally administered with 50 μg/kg of SFN; an experimental group (BLM+MET) that was administered with BLM and orally administered with 25 mg/hg of Met; and an experimental group (BLM+SFN+MET) that was administered with BLM and orally administered with 50 μg/kg of SFN and 25 mg/kg of Met. At this time, C57BL/6 mice were administered with 2.5 unit of BLM by intratracheal injection under anesthesia at the experiment initiation day and 14 days, and the mice were administered with SFN and Met every day during the experimental period from the next day after the first administration of BLM, and the mice of the control group and experimental groups were raised for 28 days after the experiment initiation day.

Example 2: Histological Examination of Experimental Animals Induced to have Pulmonary Fibrosis and Administered with Each of Therapeutic Agents The animal models of the control group and the experimental groups that were prepared in Example 1 and raised for 28 days were sacrificed. The lung tissues were removed from these animal models, and, then fixed. The fixed lung tissues were stained by the H&E staining method and the Masson-trichrome staining method, and the stained lung tissues were evaluated by Image J assay to assess and compare lung damage and lung fibrosis (FIGS. 1a to 1c).

As shown in FIG. 1a, compared to the level of fibrous tissue found in the normal control group, the damaged fibrous regions that was stained in deep red by H&E staining and in blue by fibrous tissue-specific Masson-trichrome staining were increased in the BLM-treated lung tissue, but the size of the damaged, fibrous regions was reduced by single treatment of SFN and Met or by co-treatment thereof. Specifically, a statistically significant reduction in the level of fibrous tissue was observed in the experimental group (BLM+SFN) treated with BLM and SFN. The level of fibrous tissue was slightly reduced in the experimental group (BLM+MET) treated with BLM and Met, which was not statistically significant. The statistically significant lowest level of fibrous tissue was observed in the experimental group (BLM+SFN+MET) treated with BLM, SFN and Met.

These results could be further confirmed from the result of quantitative analysis of the red-colored region by H&E staining (FIG. 1b) and the result of quantitative analysis of the blue-colored region by Masson-trichrome staining (FIG. 1c).

Therefore, it can be seen that the composition comprising SFN and MET has the greatest therapeutic effects on the pulmonary fibrosis-induced animals.

Example 3: Western Blot and ELISA

The animal models of the control group and the experimental groups that were prepared in Example 1 and raised for 28 days were sacrificed. The lung tissues and serum samples were obtained from these animal models. Then, the samples were subjected to Western blot analysis for TGF-β1 (transforming growth factor β1) and fibronectin that are known as the key markers for pulmonary fibrosis, and also Western blot analysis and ELISA for AGE (advanced glycation end products) that shows a high level in BLM-induced lung injury and idiopathic pulmonary fibrosis in previous reports.

Example 3-1: Sample Preparation

First, the lung tissue samples were prepared by sacrificing the animal models of the control group and the experimental groups, removing the lung tissues therefrom, firing the lung tissues in formalin, processing them into tissue sections, and then staining the tissue sections.

Next, the serum, samples were prepared by sacrificing the animal models of the control group and the experimental groups, collecting the blood from the vena cava, and then obtaining the serum, from the blood.

Example 3-2: Western Blot Analysis for TGF-β1

Western blot analysis was carried, out for TGF-β1 which is a key cytokine that plays a critical role in pulmonary fibrosis and of which level increases in progressive pulmonary fibrosis (FIG. 2). FIG. 2 is a photograph snowing the result of Western blot analysis for TGF-β1 in the lung tissue samples and the serum samples of the experimental animals that were induced to nave pulmonary fibrosis and administered with each of the therapeutic agents. As shown in FIG. 2, compared to the experimental group (BLM) treated with BLM alone, the experimental group (SFN) treated with BLM and SFN and the experimental group (MET) treated with BLM and Met showed the reduced TGF-β1 levels, and the experimental group (MET+SFN) treated with BLM, SFN and Met showed the lowest TGF-β1 levels.

Example 3-3: Western Blot Analysis for Fibronectin

Fibronectin is a major product generated in various fibresis-induced tissues comprising pulmonary fibrosis, and its level is known to remarkably increase in the lung tissues by induction of pulmonary fibrosis. For this reason, Western blot analysis for fibronectin was carried out (FIG. 3). FIG. 3 is a photograph showing the result of Western blot analysis for fibronectin in the lung tissue samples and the serum samples of the experimental animals that were induced to have pulmonary fibrosis and administered with each of the therapeutic agents. As shown in FIG. 3, compared to the experimental group (BLM) treated with BLM alone, the experimental group (SFN) treated with BLM and SFN and, the experimental group (MET) treated with BLM and Met showed the reduced fibronectin levels, and the experimental group (MET+SFN) treated with BLM, SFN and Met showed the lowest fibronectin levels, which are consistent with the results of TGF-β1 analysis shown in the FIG. 2.

Example 3-4: Western Blot Analysis and ELISA for AGE

AGE is known to increase in the BLM-induced lung injury and idiopathic pulmonary fibrosis (IPF), and therefore, Western blot analysis for AGE, Ponceau staining, and ELISA were carried out (FIG. 4). FIG. 4 is a photograph showing the result of Western blot analysis (A) for AGE, a photograph showing the result of Ponceau staining (B), and a photograph showing the result of ELISA (C) in the lung tissue samples and serum samples of the experimental animals that were induced to have pulmonary fibrosis and administered with each of the therapeutic agents. As shown in FIG. 4, compared to the control group, the experimental group (BLM) treated, with BLM alone snowed the remarkably increased AGE level, the experimental group (MET) treated with BLM and Met showed, the slightly reduced AGE level, which was not significant, the experimental group (SFN) treated with BLM and SFN also showed the reduced. AGE level, which was also not statistically significant. The experimental group (MET+SFN) treated with BLM, Met and SFN snowed a significant reduction in the AGE level, indicating that the experimental group (MET+SFN) co-treated with Met and SFN is the most effective for AGE reduction.

Taken together, the results of Examples 3-2 to 3-4 suggest that single treatment of SFN or Met shows unstable therapeutic effects, whereas the combined treatment of SFN and Met snows stable therapeutic effects on BLM-induced pulmonary fibrosis in terms of the levels of the pulmonary fibrosis markers.

EFFECT OF THE INVENTION

A pharmaceutical composition comprising an isothiocyanate-based compound and a biguanide agent as active ingredients of the present invention can be used to stably prevent or treat pulmonary fibrosis for which improvement through treatment of pulmonary fibrosis.

What is claimed is:

1. A method for treating pulmonary fibrosis, comprising the step of:
   (a) administering a pharmaceutical composition for treating pulmonary fibrosis comprising a sulforaphane and a metformin as active ingredients to a subject who has pulmonary fibrosis; or
   (b) administering a pharmaceutical composition comprising the sulforaphane and a pharmaceutical composition comprising the metformin sequentially or in reverse order or simultaneously to a subject who is suspected of having pulmonary fibrosis or has pulmonary fibrosis;
   wherein the sulforaphane is administered at a concentration of 10 to 20 μM and the metformin is administered at a concentration of 10 to 20 mM.

2. The method according to claim 1, wherein the composition comprising the sulforaphane and the composition comprising the metformin are administered at the same time.

3. The method according to claim 1, wherein the administration dose of the pharmaceutical composition comprising the sulforaphane and the metformin is approximately 1 μg/kg/day to 100 mg/kg/day.

4. The method according to claim 1, wherein the administration dose of the pharmaceutical composition comprising the sulforaphane is approximately 1 to 200 μg/kg/day.

5. The method according to claim 1, wherein the administration dose of the pharmaceutical composition comprising the metformin is approximately 10 to 100 mg/kg/day.

6. The method according to claim 1, wherein the mixing ratio of the sulforaphane and the metformin comprised in the pharmaceutical composition comprising the isothiocyanate-based compound and the biguanide agent is 1:200 to 1:600 (w/w).

7. The method according to claim 1, wherein in step (b), the pharmaceutical composition comprising the sulforaphane and the pharmaceutical composition comprising the metformin are administered in a ratio of 1:200 to 1:600 (w/w), based on the weights of the active ingredients.

8. The method according to claim 1, wherein the composition further comprises a pharmaceutical acceptable carrier, excipient, or diluent.

9. The method according to claim 1, wherein in step (a), the content of the sulforaphane is 0.0001 to 0.1% by weight, based on the total weight of the composition.

10. The method according to claim 1, wherein in step (a), the content of the metformin is 0.02 to 80% by weight, based on the total weight of the composition.

* * * * *